US008039249B2

(12) United States Patent
Wo et al.

(10) Patent No.: US 8,039,249 B2

(45) **Date of Patent: *Oct. 18, 2011**

(54) COMPACT DISK BASED PLATFORM FOR SEPARATING AND DETECTING IMMUNOMAGNETIC BEAD LABELED CELLS

(75) Inventors: Andrew M. Wo, Taipei (TW); Chen-Lin Chen, Taipei (TW); Ken-Chao Chen, Taipei (TW); Yu-Cheng Pan, Taipei (TW)

(73) Assignee: National Taiwan University, Taipei (TW)

( * ) Notice: Subject to any disclaimer, the term of this patent is extended or adjusted under 35 U.S.C. 154(b) by 186 days.

This patent is subject to a terminal disclaimer.

(21) Appl. No.: 12/382,844

(22) Filed: Mar. 25, 2009

(65) Prior Publication Data

US 2010/0151560 A1 Jun. 17, 2010

(30) Foreign Application Priority Data

Dec. 12, 2008 (TW) ............................... 97148520 A

(51) Int. Cl.
*C12M 1/34* (2006.01)

(52) U.S. Cl. ................ 435/287.2; 435/287.1; 435/287.3

(58) Field of Classification Search .............. 422/65–72, 422/100–102; 435/287.1–287.3
See application file for complete search history.

(56) References Cited

U.S. PATENT DOCUMENTS 5,565,105 A 10/1996 Thakor
6,297,062 B1 10/2001 Gombinski
6,723,510 B2 4/2004 Lubenow et al.
6,806,605 B1 * 10/2004 Gabrys ........................ 310/90.5
7,094,354 B2 8/2006 Pugia et al.
2005/0221281 A1 * 10/2005 Ho .................................. 435/4
2008/0056949 A1 * 3/2008 Lee et al. ........................ 422/72

OTHER PUBLICATIONS

Xiaodong Tong, Ying Xiong, Maciej Zborowski, Sherif S. Farag, Jeffrey J. Chalmers; A Novel High Throughput Immunomagnetic Cell Sorting System for Potential Clinical Scale Depletion of T Cells for Allogeneic Stem Cell Transplantation; Experimental Hematology 35 (2007), pp. 1613-1622.

Youngho Kim, Su Hong and Sang Ho Lee, Kangsun Lee and Seok Yun, Yuri Kang, Keong-Kap Paek, Byeong-Kwon Ju, Byungkyu Kim; Novel Platform for Minimizing Cell Loss on Separation Process: Droplet-based Magnetically Activated Cell Separator; Review of Scientific Instruments 78, 07403-1-07403-7.

Jerry M. Chen, Po-Chun Huang, Mou-Gee Lin; Analysis and Experiment of Capillary Valves for Microfluidics on a Rotating Disk; Microfluid Nanofluid (2008) 4:427-437.

(Continued)

*Primary Examiner* — Michael Marcheschi
*Assistant Examiner* — Shanta G Doe
(74) *Attorney, Agent, or Firm* — Rosenberg, Klein & Lee

(57) ABSTRACT

Disclosed is a disk based platform for separating and detecting cells that are labeled with immunomagnetic beads. A disk-like carrier board forms therein at least one flow channel structure, which includes an inner reservoir for receiving a sample fluid, an outer reservoir, and a plurality of micro flow channels arranged between and in fluid communication with the inner and outer reservoirs. When the disk-like carrier board spins, cells labeled with immunomagnetic beads are attracted by a magnetic attraction unit that is arranged above the disk-like carrier board and adjacent to the inner reservoir to thereby remain in the inner reservoir, and cells that are not so labeled are acted upon by a centrifugal force induced by the spinning of the disk-like carrier board to flow with the sample fluid from the inner reservoir through the micro flow channels into the outer reservoir.

6 Claims, 8 Drawing Sheets

OTHER PUBLICATIONS

Katharina Pachmann, Oumar Camara, Andreas Kavallaris, Sabine Krauspe, Nele Malarski, Mieczyslaw Gajda, Torsten Kroll, Cornelia Jorke, Ulrike Hammer, Annelore Altendorf-Hofmann, Carola Rabenstein, Ulrich Pachmann, Ingo Runnebaum, Klaus Hoffken; Monitoring the Response of Circularing Epithelial Tumor Cells to Adjuvant Chemotherapy in Breast Cancer Allows Detection of Patients at Risk of Early Relapse; Journal of Clinical Oncology; vol. 28, No. 8, Mar. 10, 2008, pp. 1208-1215.

Katherine H. Rak Tzaczuk, Olga Goloubeva, Nancy S. Tait, Faye Feldman, Ming Tan, Zhao-Ping Lum, Stephen A. Lesko, David A. Van Echo, Paul O.P. Ts'O; The Significance of Circulating Epithelial Cells in Breast Cancer Patients by a Novel Negative Selection Method; Breast Cancer Res Treat (2008) 111: 355-364.

Jens Ducree; Stefan Haeberie; Sascha Lutz; Sarah Pausch; Felix Von Stetten; Roland Zengerle; The Centrifugal Microfluidic Bio-Disk Platform; Journal of Micromechanics and Microengineering 17 (2007) S103-S115.

Nicole Pamme; Continuous Flow Separations in Microfluidic Devices; Lab Chip, 2007, 7, 1644-1659.

Patrizia Paterlini-Brechot, Naoual Linda Benali; Circulating Tumor Cells (CTC) Detection: Clinical Impact and Future Directions; Cancer Letters; 2006.12.014, pp. 180-204.

Sungyoung Choi, Seungjeong Song, Chulhee Choi, Je-Kyun Park; Continuous Blood Cell Separation by Hydrophoretic Filtration; Lab Chip, 2007, 7, 1532-1538.

Sunitha Nagrath, Lecia V. Seouist, Shyamala Maheswaran, Daphne W. Bell, Daniel Irma, Lindsey Ulkus, Matthew R. Smith. Eunice L Kwak, Subba Digumarthy, Alona Muzikansky, Paula Ryan, Ulysses J. Balis, Ronald G. Tompkins, Daniel A. Haber, Mehmet Toner; Isolation of Rare Circulating Tumour Cells in Cancer Patients by Microchip Technology; Nature, vol. 450, Dec. 20/27, 2007, pp. 1235-1241.

Kara E. McCloskey, Jeffrey J. Chalmers, Maciej Zborowski; Magnetic Cell Separation: Characterization of Magnetophoretic Mobility; Analytical Chemistry, vol. 75, No. 24, Dec. 15, 2003, pp. 6868-6874.

Oscar Lara, Xiaodong Tong, Maciej Zborowski, Jeffrey J. Chalmers, Enrichment of Rare Cancer Cells Through Depletion of Normal Cells Using Density and Flow-Through, Immunomagnetic Cell Separation; Experimental Hematology 32 (2004) 891-904.

T. Fehm, EF Solomayer, S. Meng, T. Tucker, N. Lane, J. Wang, G. Gebauer; Methods for Isolating Circulating Epithelial Cells and Criteria for Their Classification as Carcinoma Cells; Cytotherapy (2005) vol. 7, No. 2, 171-185.

David W. Inglis, Robert Riehn, James C. Sturm, Robert H. Austin; Microfluidic High Gradient Magnetic Cell Separation; Journal of Applied Physics 99, 08K101-1-08K101-3.

Marc Madou, Jim Zoval, Guangyao Jia, Horacio Kido, Jitae Kim, Nahui Kim; Lab on a CD; arjournals.annualreviews.org, National Taiwan University, Jun. 19, 2008; pp. 601-627.

J. Steigert, T. Brenner, M. Grumann, L. Riegger, S. Lutz, R. Zengerle, J. Ducree; Integrated Siphon-Based Metering and Sedimentation of Whole Blood on a Hydrophilic Lab-on a Disk; Biomed Microdevices (2007) 9:675-679.

Stefan Miltenyi; Werner Muller; Walter Weichel; Andreas Radbruch; High Gradient Magnetic Cell Separation with MACS; Cytometry 11:231-238 (1990).

Yoichiro Ito, Kazufusa Shinomiya; A New Continuous-Flow Cell Separation Method Based on Cell Density: Principle, Apparatus, and Preliminary Application to Separation of Human Buffy Coat; Journal of Clinical Apheresis 16:186-191 (2001).

* cited by examiner

COMPACT DISK BASED PLATFORM FOR SEPARATING AND DETECTING IMMUNOMAGNETIC BEAD LABELED CELLS

FIELD OF THE INVENTION

The present invention relates to a cell separation device, and in particular to a compact disk based platform for separating and detecting cells labeled with immunomagnetic beads.

BACKGROUND OF THE INVENTION

Detection and quantification of cancer cells or rare cells present in body fluids are regarded as a potential indicator for clinical diagnoses, prognostication, and biomedicine research. For example, circulating tumor cells (CTC) are rare in the blood of patients with metastatic cancer, and it is possible to monitor the response of CTC to adjuvant therapy. To detect and quantify the rare cells present in fluids, the rare cells must be first separated. Thus, cell separation techniques are developed.

Various cell separation techniques are now available, including fluorescence activated cell separation (FACS), dielectrophoresis (DEP) cell separation, separation techniques that employ massively parallel microfabricated sieving devices, magnetically activated cell separation (MACS), and other techniques that uses optics and acoustics. Among these cell separation techniques, FACS and MACS are most often used.

Although it is often used, FACS suffers several drawbacks, including high cost, difficult disinfection, and consuming a great amount of sample. Contrary to FACS, MACS is efficient to obtain a major quantity of the target cells in a short period and reduces the consumption of the sample. However, these cells must be transferred to a slide or an observation platform before they can be observed with a microscope. Such a process of transfer often leads to a great cell loss.

U.S. Pat. No. 5,565,105 discloses a magnetocentrifugation method, wherein charged particles are deposited in a rotor board and a magnetic field is vertically applied to the rotor board, whereby when the rotor board is brought into rotation, the charged particles contained in the rotor board are moved within the magnetic field, and are thus acted upon by Lorentz force to separate from non-charged particles.

U.S. Pat. No. 6,297,062 discloses a method for separating at least one species of biological entities from a sample solution. Each species being a first member of a pair forming group, from a sample solution by contacting the sample solution with a matrix of magnetic particles wherein each magnetic particle in the matrix is coupled to the second member of the pair forming group. The matrix should contain magnetic particles, coupled to several different species of second members of the pair forming groups. When the sample is contacted with said matrix, and each species of biological entities, binds to its specific second member of the pair forming group which is present in a discrete location, from the other entities, and due to the magnetic properties of the magnetic particles, each species may be obtained separately.

U.S. Pat. No. 6,723,510 discloses a method for separating particles with minimized particle loss, wherein a detergent containing matrix beads are bound with a sample containing target particles so as to reduce the loss of the target particles in the separation processes.

U.S. Pat. No. 7,094,354 discloses a microfluidic device provides separation of particles in a liquid sample, particularly, separation of a sample of whole blood into its components for further analysis. Separation into red blood sample has been transferred into a separation chamber with the application of centrifugal force of less than about five times gravity. When blood in the sample, a separation chamber for receiving the sample and separating it into its fractions using low gravitational forces, and vents for removing the air displaced by blood and its fractions.

SUMMARY OF THE INVENTION

In view of the above described, FACS needs a high cost system and requires extended time in operation and MACS is effective in obtaining a major portion of target cells and thus reduces the operation time for sampling in doing analysis. However, MACS may suffer the disadvantage of high cell loss.

Thus, an objective of the present invention is to provide a compact disk based platform for separating and detecting cells labeled with immunomagnetic beads, which is low cost, is easy to perform detection and observation, and has reduced cell loss, and which is applicable to separate at least two cells that are respectively labeled and not labeled with the immunomagnetic beads.

The solution adopted in the present invention to overcome the problems of the conventional techniques is a disk-like carrier board and a magnetic attraction unit, wherein the disk-like carrier board forms at least one flow channel structure, which comprises an inner reservoir, an outer reservoir, and a plurality of micro flow channels. The inner reservoir is arranged adjacent to a geometric center of the disk-like carrier board for receiving a sample fluid, which contains at least two cells that are respectively labeled and not labeled with immunomagnetic beads. The outer reservoir is arranged adjacent to an outer circumferential rim of the disk-like carrier board. The plurality of micro flow channels is arranged between and in fluid communication with the inner and outer reservoirs. The magnetic attraction unit is arranged above the disk-like carrier board and adjacent to the inner reservoir to generate a magnetic force having a predetermined distribution of intensity.

The solution adopted in the present invention is effective in maintaining the cells labeled with immunomagnetic beads in the inner reservoir by using the magnetic force and allowing the cells that are not labeled with immunomagnetic beads to move to the outer reservoir by means of a centrifugal force so as to separate the cells that are labeled with the immunomagnetic beads.

Further, the compact disk based platform for separation and detection of immunomagnetic bead labeled cells can be easily manufactured by means of for example laser machining, CNC machining, micromachining, or injection molding and the material that is used to make the platform can be easily acquired, thereby offering an advantage of low cost manufacturing.

Further, the cells that are not labeled with immunomagnetic beads can be directly collected in collection bins to allow an operator to carry out direct observation without transferring the cells to a slide or an observation platform. This makes the observation easy and, due to no transfer of cell needed, cell loss can be minimized.

BRIEF DESCRIPTION OF THE DRAWINGS

The present invention will be apparent to those skilled in the art by reading the following description of the preferred embodiments of the present invention, with reference to the attached drawings, in which.

DETAILED DESCRIPTION OF THE PREFERRED EMBODIMENTS

Figure 1:
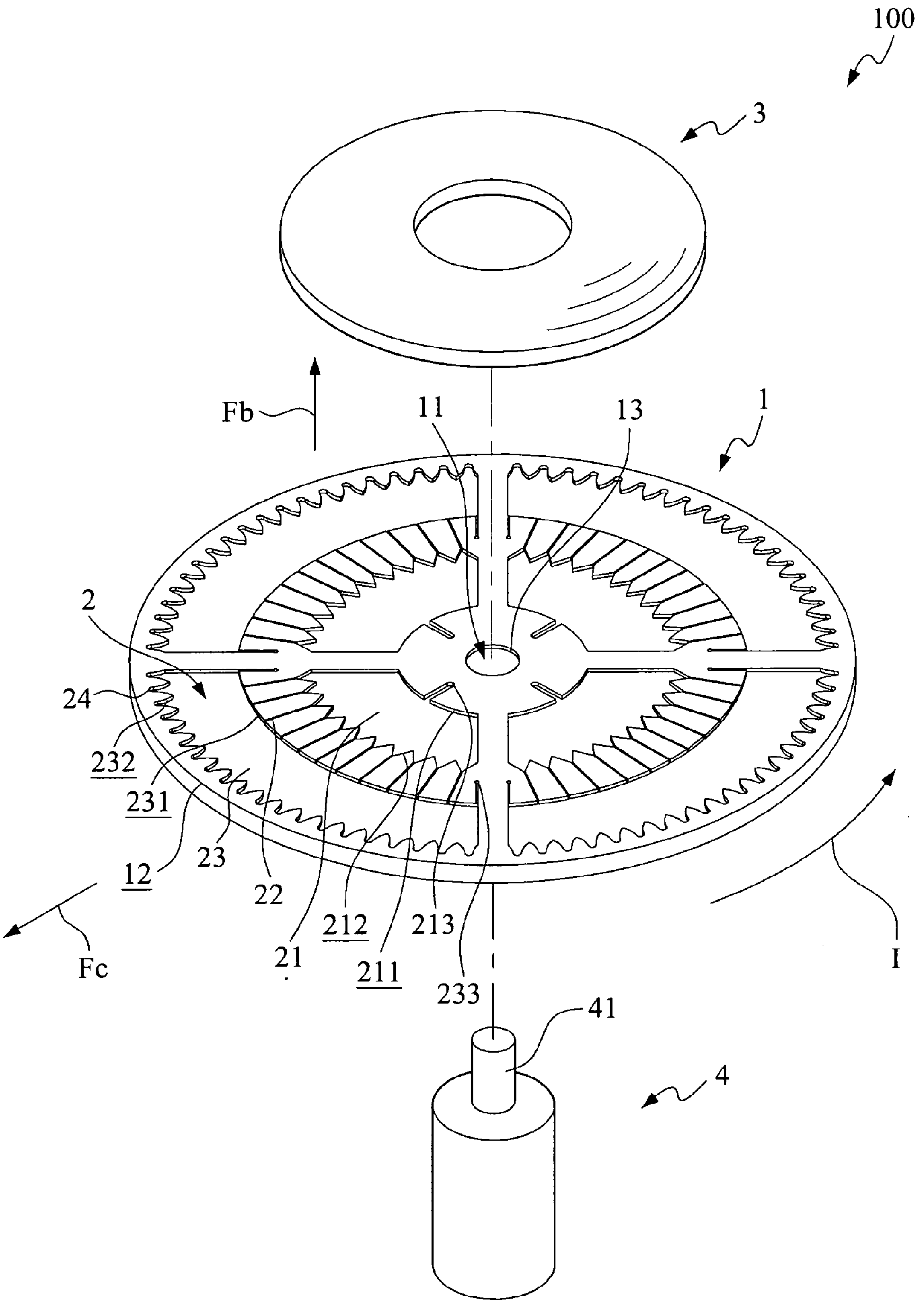
FIG. 1 is a perspective view of a first embodiment of the present invention in an exploded form.

With reference to the drawings and in particular to FIG. 1, which shows a perspective view of a first embodiment of the present invention, the present invention provides a compact disk (CD) based platform for separating and detecting immunomagnetic bead labeled cells, which is generally designated at 100. The platform 100 comprises a disk-like carrier board 1 in which at least one flow channel structure 2 is formed for separating at least two cells contained in a sample fluid by using a magnetic force induced by a magnetic attraction unit 3 and a centrifugal force induced by the spinning of the carrier board 1 by a driving device 4.

Figure 2:
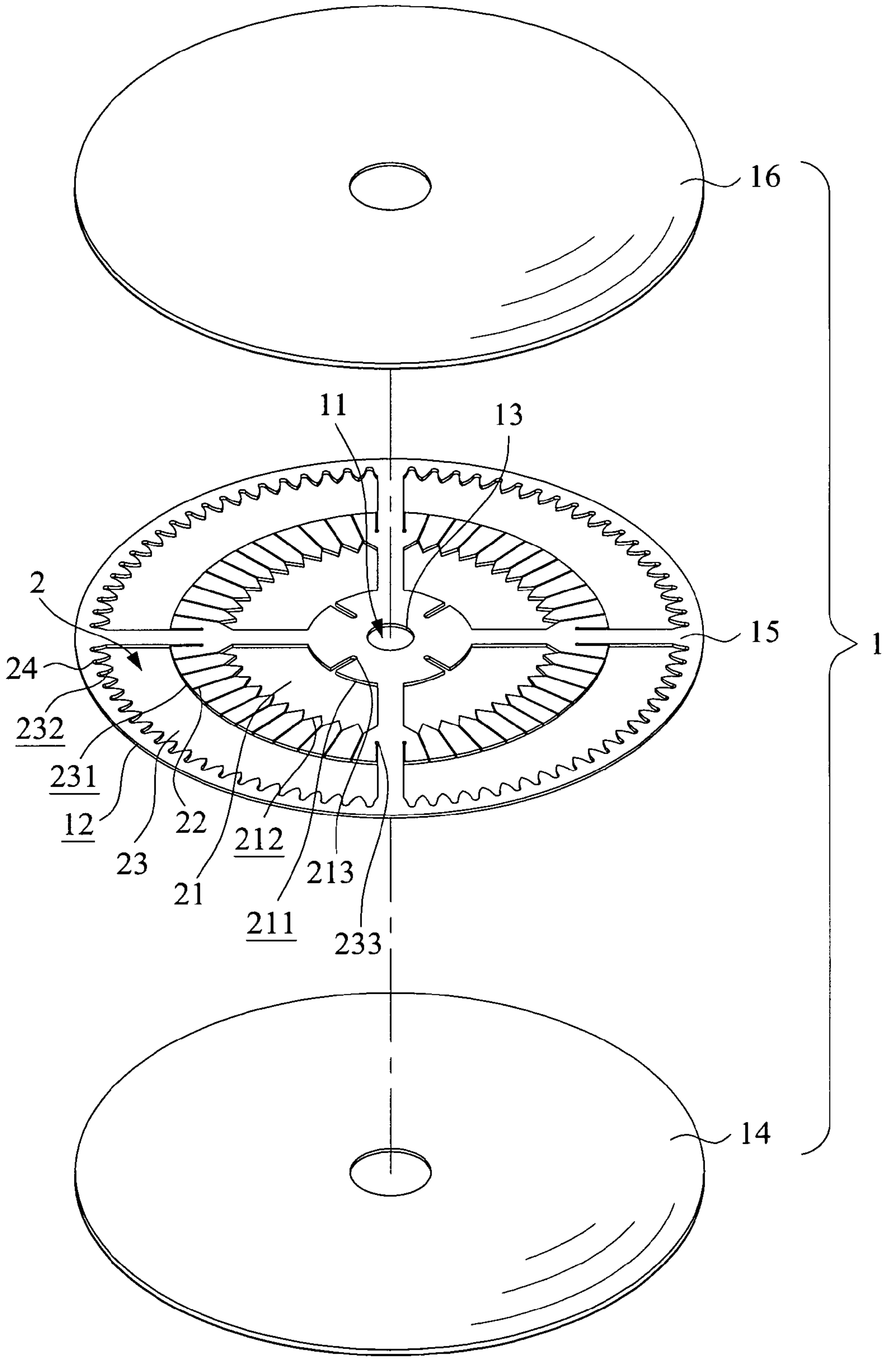
FIG. 2 is an exploded view of a disk-like carrier board in accordance with the first embodiment of the present invention.

Also referring to FIG. 2, which shows an exploded view of the disk-like carrier board in accordance with the first embodiment of the present invention, the disk-like carrier board 1 has a geometric center 11 and an outer circumferential rim 12. A central hole 13 is defined at the geometric center 11 and the central hole 13 functions to couple to a spindle 41 of the driving device 4. In the instant embodiment, the disk-like carrier board 1 has a three-layer configuration, which includes, from the bottom side to the top side, a bottom base layer 14, a middle, flow channel structure layer 15, and a top cover layer 16.

The flow channel structure 2 is formed in the flow channel structure layer 15 of the disk-like carrier board 1. In the instant embodiment, the base layer 14 and the flow channel structure layer 15 are made of acrylic resins, such as polymethylmethacrylate (PMMA) and the cover layer 16 is comprised of a layer of a thin film. The flow channel structure layer 15 is processed by $CO_2$ laser machining to form the flow channel structure 2 and is then bound to the base layer 14. Thereafter, the cover layer 16 is applied atop the flow channel structure layer 15 to completely cover and enclose the flow channel structure 2. This way is advantageous by being easy to manufacture, using low cost materials, and reducing manufacturing costs.

Apparently, the flow channel structure layer 15 can alternatively be formed as a multiple-layered structure including multiple plates stacked and bound together. Further, the disk-like carrier board 1 can be alternatively made a single-layered structure and the material used is not limited to acrylic reins. The flow channel structure 2 can alternatively formed by employing machining techniques other than laser machining, such as CNC machining, micromachining, and injection molding.

Figure 3:
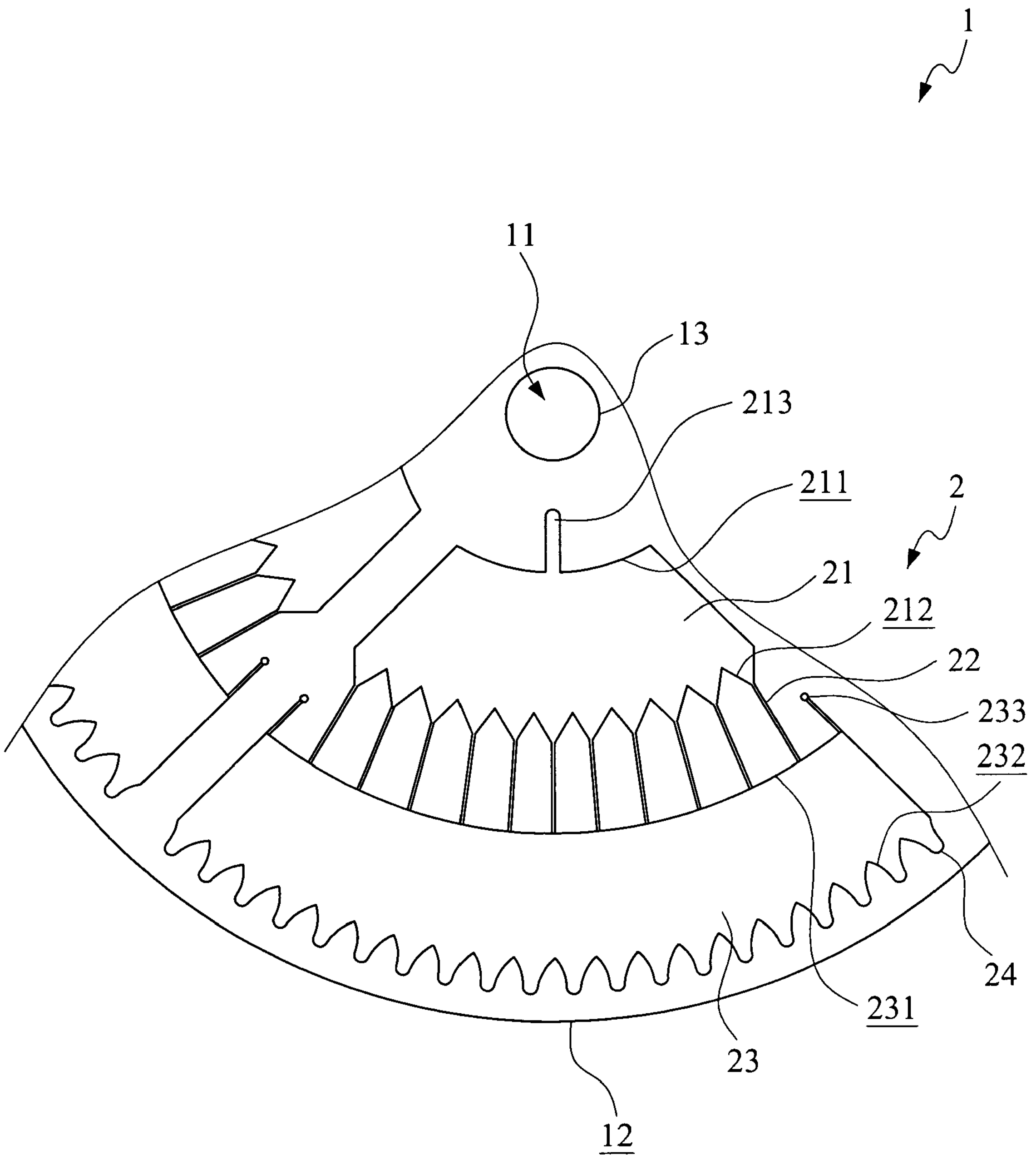
FIG. 3 is a top plan view of a portion of the disk-like carrier board in accordance with the first embodiment of the present invention.

Also referring to FIG. 3, which shows a top plan view of a portion of the disk-like carrier board in accordance with the first embodiment of the present invention, in the instant embodiment, the disk-like carrier board 1 forms four flow channel structures 2. Each flow channel structure 2 comprises an inner reservoir 21, a plurality of micro flow channels 22, and an outer reservoir 23, which are sequentially arranged in a direction from the geometric center 11 of the disk-like carrier board 1 toward the outer circumferential rim 12.

The inner reservoir 21 has an inner bank 211, which is adjacent to the geometric center 11 of the disk-like carrier board 1, and an outer bank 212, which is in fluid communication with the micro flow channels 22. In the inner bank 211 of the inner reservoir 21, a fluid inlet opening 213 is defined and extends in a direction toward the geometric center 11 of the disk-like carrier board 1.

The outer reservoir 23 also has an inner bank 231, which is in fluid communication with the micro flow channels 22, and an outer bank. 232, which is adjacent to the outer circumferential rim 12 of the disk-like carrier board 1. In the instant embodiment, the inner bank 231 of the outer reservoir 23 forms at least one vent hole 233. The outer bank 232 defines a plurality of collection bins 24.

In the instant embodiment, the magnetic attraction unit 3 comprises a magnetic ring; alternatively, it can be replaced by an array of magnets that are properly arranged. Various magnets, such as permanent magnets and electromagnets, can be used. The magnetic attraction unit 3 is arranged above the disk-like carrier board 1 and close to the central hole 13 of the disk-like carrier board 1 to generate a magnetic force Fb having a predetermined distribution of intensity.

In the instant embodiment, the driving device 4 is arranged below the disk-like carrier board 1 and the spindle 41 is operatively coupled to the central hole 13 of the disk-like carrier board 1 for spinning the disk-like carrier board 1.

Figure 4:
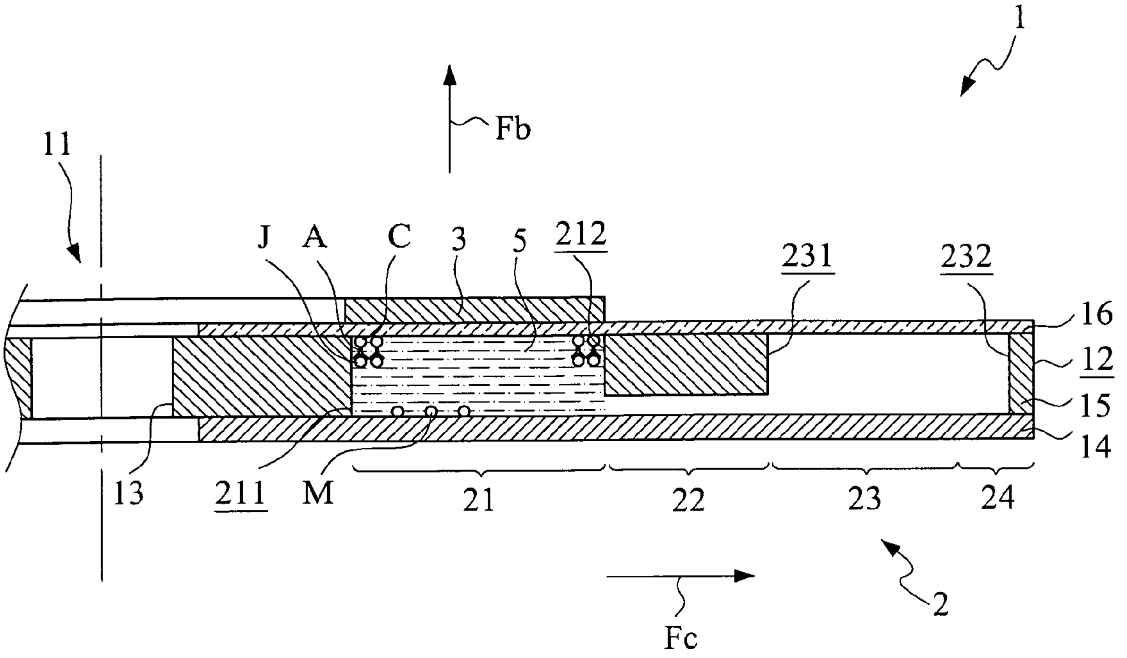
FIG. 4 is a schematic cross-sectional view illustrating the disk-like carrier board of the first embodiment before being driven to spin.
Figure 5:
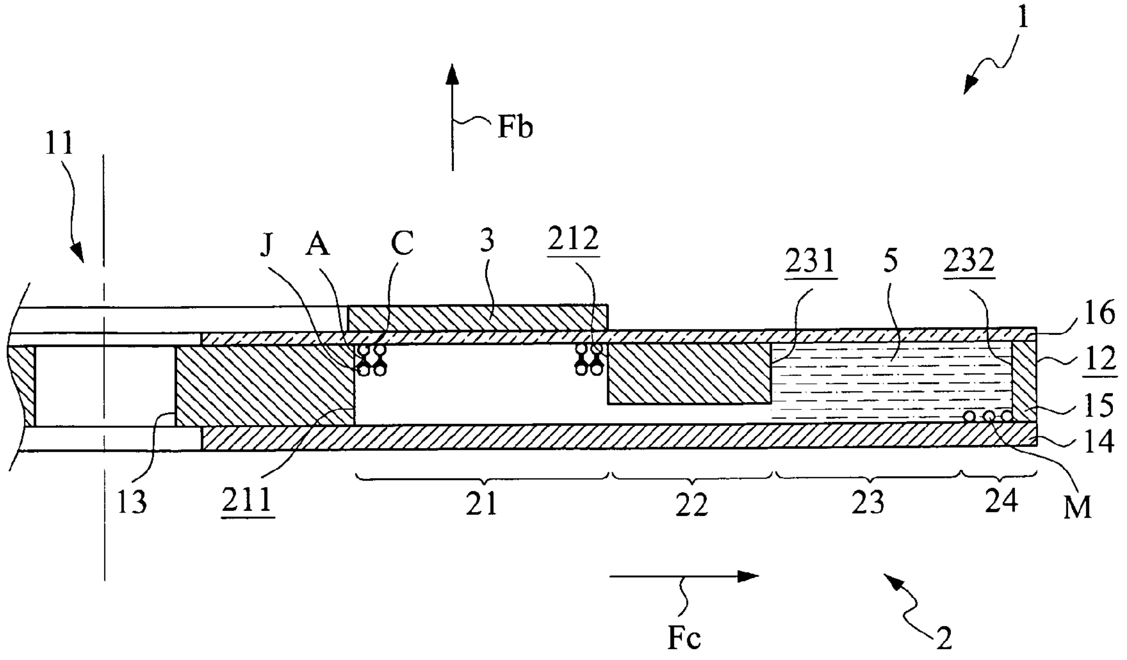
FIG. 5 is a schematic cross-sectional view illustrating the disk-like carrier board of the first embodiment after being driven to spin.

Referring to both FIGS. 4 and 5, which are schematic cross-sectional views respectively illustrating the disk-like carrier board before and after being driven to spin, and reference being also made to FIGS. 1 and 3, the operation of the first embodiment of the present invention will be explained.

A sample fluid 5 that is subjected to cell separation is introduced through the fluid inlet opening 213 into the inner reservoir 21. In the instant embodiment, the sample fluid 5 contains two cells, one being Jurkat cell (J), which is a human lymphoma cell and the other being MCF7 cell (M), which is a human breast cancer cell. The Jurkat cells J are labeled with immunomagnetic beads C that contain CD45 anti-body A. The MCF7 cells M are not labeled. It is apparent that a sample fluid containing more than two cells, of which one is labeled with immunomagnetic beads, can be used.

The disk-like carrier board 1 is driven by the driving device 4 to spin in a given spinning direction I. The sample fluid 5 is acted upon by the centrifugal force Fc induced by the spinning of the disk-like carrier board 1 and flows from the inner reservoir 21 through the micro flow channels 22 to the outer reservoir 23.

Since the Jurkat cells J contained in the sample fluid 5 are labeled with the immunomagnetic beads C, and since the immunomagnetic beads C are attracted the magnetic force Fb generated by the magnetic attraction unit 3, the Jurkat cells J will remain in the inner reservoir 21. The MCF7 cells M that are not labeled with immunomagnetic beads C are driven by the centrifugal force Fc to flow with the sample fluid 5 from the inner reservoir 21 through the micro flow channels 22 into the outer reservoir 23 to be collected in the collection bins 24.

Figure 6:
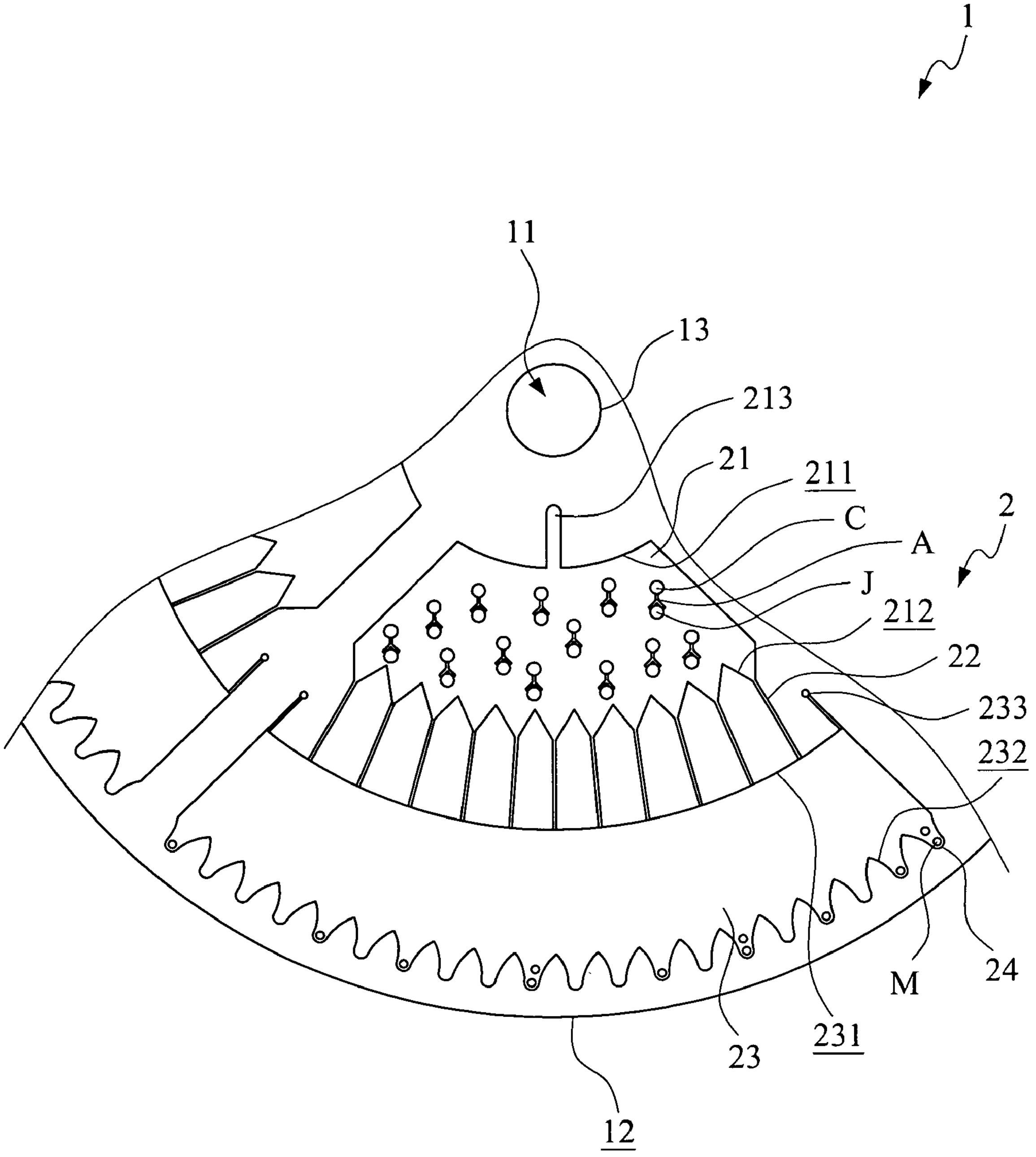
FIG. 6 is a top plan of a portion of the disk-like carrier board of the first embodiment after being driven to spin.

Referring to FIG. 6, which illustrates a top plan of a portion of the disk-like carrier board after being driven to spin, after the disk-like carrier board 1 has been driven to spin, the Jurkat cells J are retained inside the inner reservoir 21, while the MCF7 cells M are subjected to the centrifugal force Fc and collected in the collection bins 24 of the outer reservoir 23. As a result, an operator may easily carry out detection and observation on the MCF7 cells M collected in the collection bins 24.

In practical applications, the multiple flow channel structures 2 formed in the disk-like carrier board 1 allows for simultaneously performing separation, as well as subsequent detection/observation, for multiple sample fluids, whereby operation efficiency can be enhanced. In respect of detection and observation, cells to be detected/observed, such as MCF7 cells M in the instant embodiment, can be labeled with fluorescence substance in advance to enhance the observation.

Figure 7:
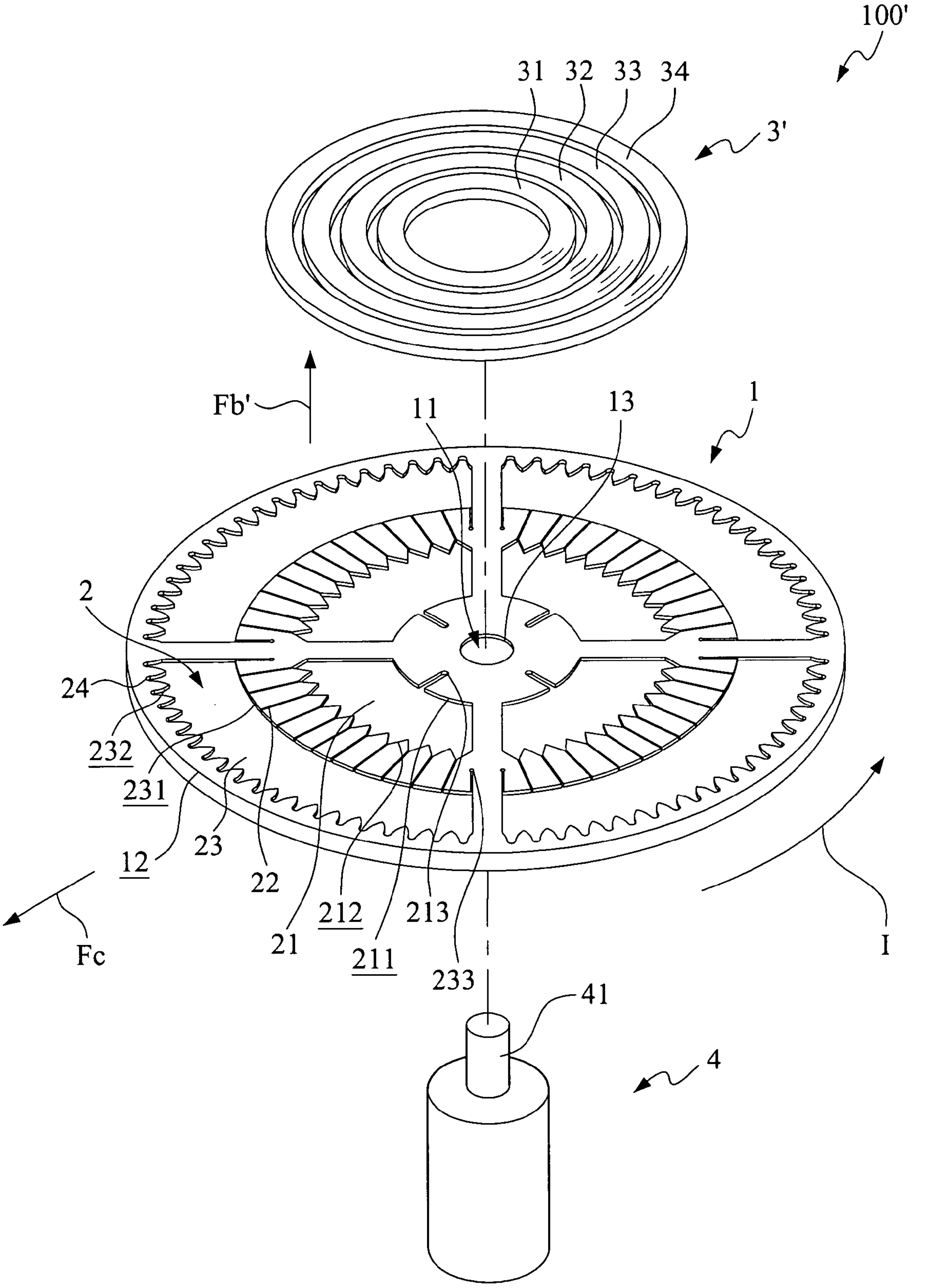
FIG. 7 is a perspective view of a second embodiment of the present invention in an exploded form.

Referring to FIG. 7, which shows a perspective view of a second embodiment of the present invention, the second embodiment provides a platform 100' for separating and detecting of cells, which has a configuration similar to that of the first embodiment. Thus, same or similar parts/components/members are labeled with the same reference numerals for correlation therebetween. The difference residing between the first and second embodiments is that the magnetic attraction unit 3' of the second embodiment comprises a plurality of concentric magnetic rings 31, 32, 33, 34 to generate a magnetic force Fb' of a magnetic field having a high magnetic gradient.

Figure 8:
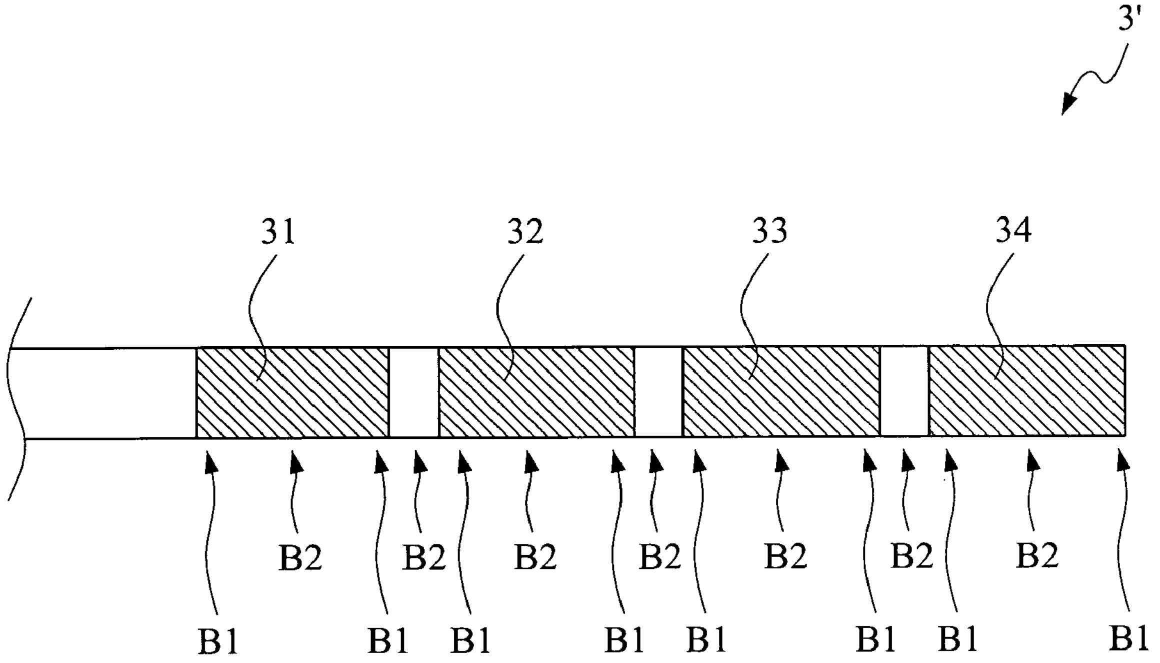
FIG. 8 is a schematic cross-sectional view of a magnetic attraction unit in accordance with the second embodiment of the present invention, demonstrating the distribution of the magnetic force generated thereby.

Referring to FIG. 8, which shows a schematic cross-sectional view of the magnetic attraction unit in accordance with the second embodiment of the present invention, wherein the distribution of magnetic force generated by the magnetic attraction unit is demonstrated, the magnetic attraction unit 3' comprises a plurality of concentric magnetic rings 31, 32, 33, 34 and each magnetic ring 31, 32, 33, 34 has opposite edge portions that are relatively strong magnetic force zones B1 and a central portion that is a relatively weak magnetic force zone B2. With the arrangement of the multiple magnetic rings, more edge portions are provided to exhibit a magnetic force of a magnetic field having a high magnetic gradient and enhanced magnetic attraction is realized.

Figure 9:
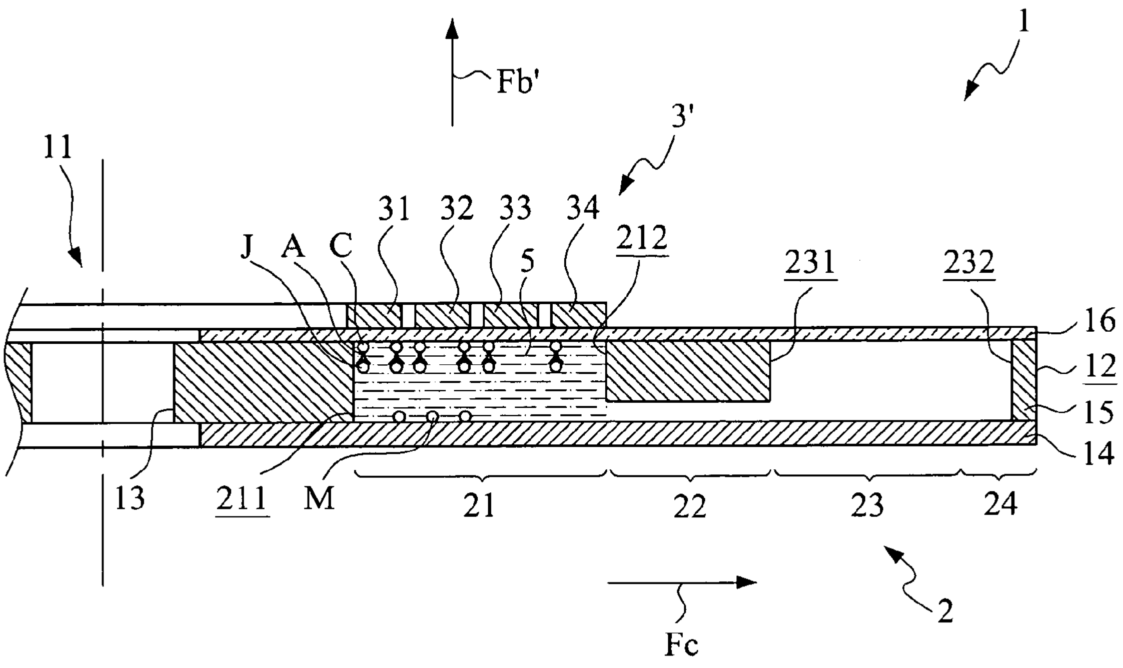
FIG. 9 is a schematic cross-sectional view illustrating a disk-like carrier board of the second embodiment before being driven to spin.
Figure 10:
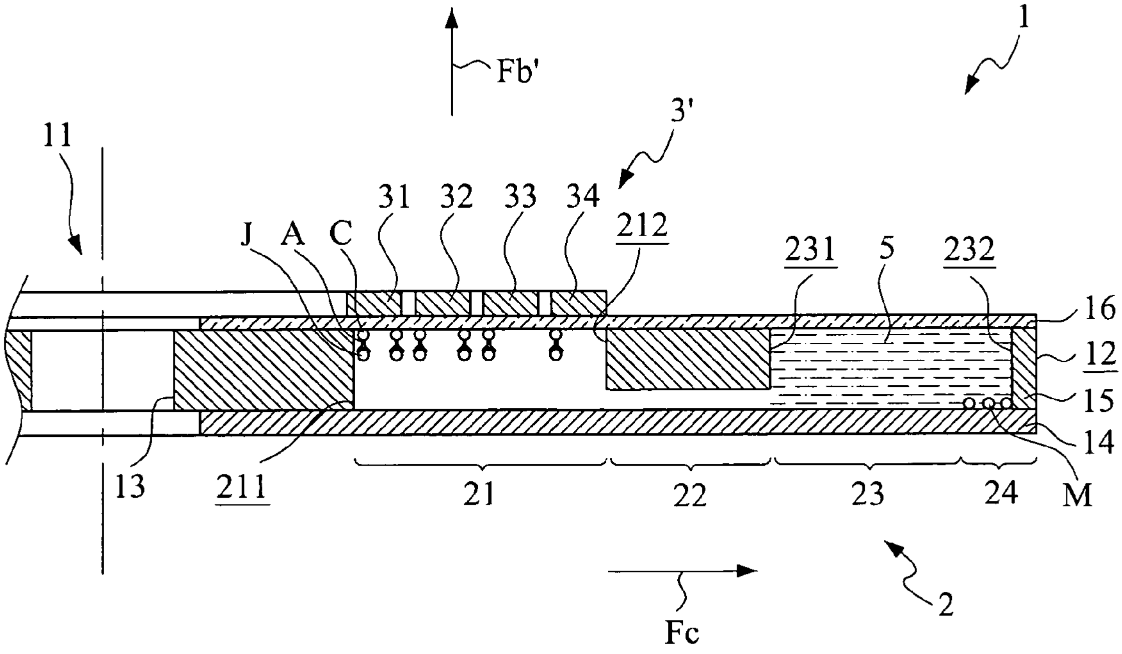
FIG. 10 is a schematic cross-sectional view illustrating the disk-like carrier board of the second embodiment after being driven to spin.

Referring to both FIGS. 9 and 10, which are schematic cross-sectional views respectively illustrating the disk-like carrier board of the second embodiment before and after being driven to spin, and reference being also made to FIGS. 7 and 8, the operation of the second embodiment of the present invention will be explained.

When the disk-like carrier board 1 is driven by the driving device 4 to spin, the Jurkat cells J that are labeled with immunomagnetic beads C are attracted by the magnetic force Fb' generated by the magnetic attraction unit 3'. In case that some of the Jurkat cells J are not attracted and securely held by the magnetic ring 31 that is closet to the geometric center 11 of the disk-like carrier board 1, they will still be attracted and held by the magnetic rings 32, 33, 34 that are located outside the magnetic ring 31. In this way, the Jurkat cells J that are labeled with immunomagnetic beads C will be step-by-step acted upon by the magnetic forces individually generated by the sequentially arranged magnetic rings to ensure that the Jurkat cells J that are labeled with immunomagnetic beads C will be retained in the inner reservoir 21 thereby enhancing the result of separation.

Although in the preferred embodiments of the present invention, MCF7 cells M and Jurkat cells J are taken as examples for discussion purposes, the present invention is also applicable to for example fetal cell separation, cell separation for whole blood sample, separation of endothelial colony forming cells (ECFC) from umbilical cord blood (UCB).

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A disk based platform for separating and detecting at least an immunomagnetic bead labeled cell and a non-labeled cell contained in a sample fluid, comprising:

a disk-like carrier board, which has a geometric center and an outer circumferential rim, the disk-like carrier board forming at least one flow channel structure, each flow channel structure comprising:

an inner reservoir, which is arranged adjacent to the geometric center of the disk-like carrier board for receiving the sample fluid;

an outer reservoir, which is arranged adjacent to the outer circumferential rim of the disk-like carrier board; and a plurality of micro flow channels, which is arranged between and in fluid communication with the inner reservoir and the outer reservoir; and a magnetic attraction unit arranged above the disk-like carrier board and adjacent to the inner reservoir thereof, the magnetic attraction unit comprising a plurality of concentric magnetic rings disposed substantially in alignment with said inner reservoir of said disk-like carrier board, said concentric magnetic rings being radially spaced apart one from another to generate a magnetic force of a magnetic field having a prominent magnetic gradient along the radial direction of said inner reservoir;

wherein when the disk-like carrier board spins, the immunomagnetic bead labeled cell is attracted by the magnetic force generated by the magnetic attraction unit to thereby remain in the inner reservoir, and the non-labeled cell is acted upon by a centrifugal force induced by the spinning of the disk-like carrier board to flow with the sample fluid from the inner reservoir through the micro flow channels into the outer reservoir, and wherein said prominent magnetic gradient of said magnetic field enhances the separation of the immunomagnetic bead labeled cell from the non-labeled cell.

2. The platform as claimed in claim 1, wherein the disk-like carrier board further comprises a cover layer arranged thereon.

3. The platform as claimed in claim 1, wherein the disk-like carrier board comprises a base layer and at least one flow channel structure layer, the flow channel structure being formed in the flow channel structure layer.

4. The platform as claimed in claim 1, wherein the outer reservoir has an outer bank that forms at least one collection bin.

5. The platform as claimed in claim 1, wherein the flow channel structure of the disk is selectively formed by laser machining, CNC machining, micromachining, and injection molding.

6. The platform as claimed in claim 1, wherein the magnetic attraction unit comprises a magnetic element selected from a group consisting of a permanent magnet and an electromagnet.

* * * * *